US006408043B1

(12) United States Patent
Hu et al.

(10) Patent No.: US 6,408,043 B1
(45) Date of Patent: *Jun. 18, 2002

(54) VOLUMETRIC COMPUTED TOMOGRAPHY SYSTEM FOR CARDIAC IMAGING INCLUDING A SYSTEM FOR COMMUNICATING DATA OVER A NETWORK

(75) Inventors: Hui Hu; Jiang Hsieh, both of Waukesha; Stanley H. Fox; Kishore C. Acharya, both of Brookfield; Hui David He; Yi Sun, both of Waukesha, all of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/473,247

(22) Filed: Dec. 27, 1999

Related U.S. Application Data

(63) Continuation-in-part of application No. 09/307,400, filed on May 7, 1999.

(51) Int. Cl.[7] .................................................. A61B 6/00
(52) U.S. Cl. .................................. 378/8; 378/4; 378/20
(58) Field of Search .................................. 378/8, 4, 20

(56) References Cited

U.S. PATENT DOCUMENTS 6,301,324 B1 * 10/2001 Pearson et al. ............... 378/15

OTHER PUBLICATIONS

Carl Crawford and Kevin King, *Computed Tomography Scanning with Simultaneous Patient Translation*, Med. Phys. 17(6), Nov./Dec. 1990, pp. 967–982.

* cited by examiner

Primary Examiner—David P. Porta
Assistant Examiner—Pamela R. Hobden
(74) Attorney, Agent, or Firm—Foley & Lardner; Peter J. Vogel; Michael A. Della Penna (57) ABSTRACT

A method for generating an image of an object using a computed tomography (CT) imaging system, which includes at least one x-ray detector array and at least one rotating x-ray source projecting an x-ray beam, includes the steps of identifying a physiological cycle of the object (the cycle comprising a plurality of phases); selecting at least one phase of the object; collecting at least one segment of projection data for each selected phase of the object during each rotation of each x-ray source; generating a projection data set by combining the projection data segments; generating a cross-sectional image of the entire object from the projection data set; and communicating the image or data associated with the image to a remote facility. The remote facility provides remote services over a network.

30 Claims, 6 Drawing Sheets

VOLUMETRIC COMPUTED TOMOGRAPHY SYSTEM FOR CARDIAC IMAGING INCLUDING A SYSTEM FOR COMMUNICATING DATA OVER A NETWORK

CROSS REFERENCE TO RELATED APPLICATIONS

This application is a continuation-in-part (CIP) of U.S. Pat. application Ser. No. 09/307,400, entitled "VOLUMETRIC COMPUTED TOMOGRAPHY SYSTEM FOR CARDIAC IMAGING" by Hu, et al., filed on May 7, 1999.

BACKGROUND OF THE INVENTION

The present invention relates generally to the field of medical diagnostic systems, such as imaging systems. More particularly, the invention relates to a system and technique for generating images of a moving object.

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In at least one known type of imaging system, commonly known as a computer tomography (CT) system, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object.

One method for reconstructing an image from a set of projection data is referred to in the art as the filtered backprojection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed. In addition to reduced scanning time, helical scanning provides other advantages such as improved image quality and better control of contrast.

In helical scanning, and as explained above, only one view of data is collected at each slice location. To reconstruct an image of a slice, the other view data for the slice is generated based on the data collected for other views. Helical reconstruction algorithms are known, and described, for example, in C. Crawford and K. King, "Computed Tomography Scanning with Simultaneous Patient Translation," Med. Phys. 17(6), Nov/Dec 1990.

In order to generate images of a rapidly moving object, such as a heart, known imaging systems have minimized motion artifacts, caused by the movement of the heart, by utilizing a high rotational speed gantry or by incorporating electron beam technology. However, the high speed gantry system significantly increases the force applied to the x-ray source and the detector affecting performance of the system. The electron beam technology requires a very complex design that significantly increases the cost of the scanner. As a result, few systems are capable of generating images of a moving heart without generating images containing significant motion artifacts.

To generate images of a moving object, it is desirable to provide an imaging system which gathers segments of projection data of a selected phase of the object so that by combining the segments motion artifacts are minimized. It would also be desirable to provide such a system which generates a cross-sectional image of the entire object for a selected phase of the object.

Solutions to the problems described above have not heretofore included significant remote capabilities. In particular, communication networks, such as, the Internet or private networks, have not been used to provide remote services to such medical diagnostic systems. The advantages of remote services, such as, remote monitoring, remote system control, immediate file access from remote locations, remote file storage and archiving, remote resource pooling, remote recording, remote diagnostics, and remote high speed computations have not heretofore been employed to solve the problems discussed above.

Thus, there is a need for a medical diagnostic system which provides for the advantages of remote services and addresses the problems above. In particular, there is a need for remote upgrades, remote diagnostics, remote servicing, remote viewing, remote file storage, remote control, and remote adjustments to system parameters and functions. Furthermore, there is a need for contractual arrangements, such as, per use licenses which lease the medical diagnostic equipment based on use. Additionally, remote services may also include expert on-line assistance for image scanning techniques, image analysis, pathology detection, imaging unit maintenance, and other expert-aided operations.

SUMMARY OF THE INVENTION

One embodiment of the invention relates to a method for generating an image of an object using a computed tomography (CT) imaging system. The imaging system includes at least one x-ray detector array and at least one rotating x-ray source projecting an x-ray beam. The method includes the steps of identifying a physiological cycle of the object (the cycle including a plurality of phases); selecting at least one phase of the object; collecting at least one segment of projection data for each selected phase of the object during each rotation of each x-ray source; generating a projection data set by combining the projection data segments; and generating a cross-sectional image of the entire object from the projection data set.

Another embodiment of the invention relates to a computed tomography (CT) imaging system for generating an image of an object. The imaging system includes at least one x-ray detector array and at least one rotating x-ray source projecting an x-ray beam. The imaging system is configured to identify a physiological cycle of the object (the cycle including a plurality of phases); allow an operator to select at least one phase of the object; collect at least one segment of projection data for each selected phase of the object during each rotation of each said x-ray source; generating a projection data set by combining said projection data segments; and generate a cross-sectional image of the entire object from said projection data set.

Other principle features and advantages of the present invention will become apparent to those skilled in the art upon review of the following drawings, the detailed description, and the appended claims.

BRIEF DESCRIPTION OF THE DRAWINGS

Preferred exemplary embodiments are described below with reference to the accompanying drawings, wherein like reference numerals denote like elements.

DETAILED DESCRIPTION OF THE PREFERRED EMBODIMENT

Figure 1:
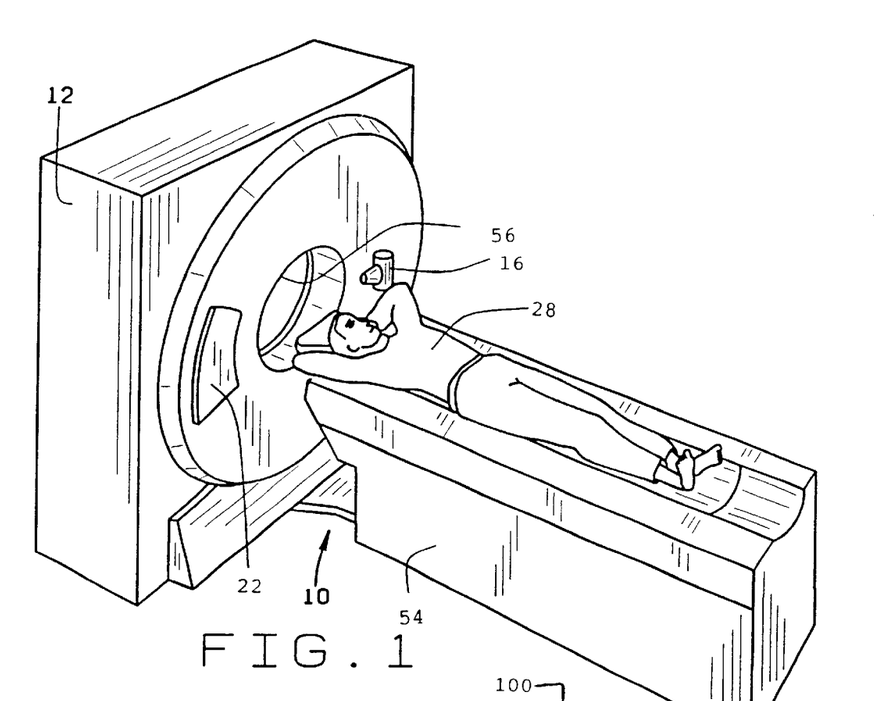
FIG. 1 is a pictorial view of a CT imaging system.
Figure 2:
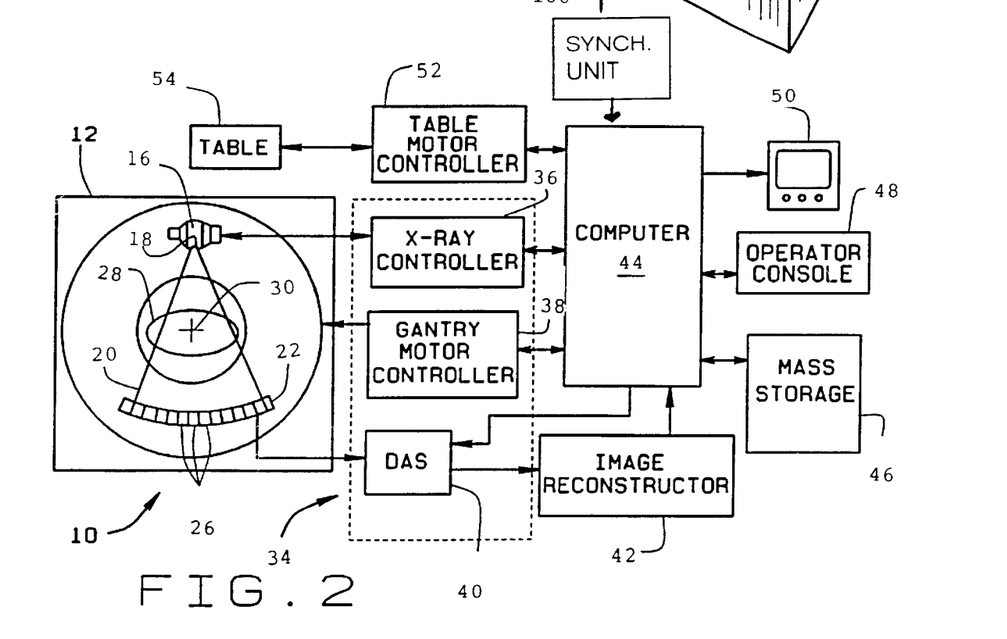
FIG. 2 is a block schematic diagram of the system illustrated in FIG. 1.

Referring to FIGS. 1 and 2, an imaging system 10 is shown as a "third generation" computed tomography (CT) imaging system including a gantry 12 having at least one rotating x-ray source 16 that projects from a focal spot 18 a beam of x-rays 20 toward a detector array 22. X-ray beams 20 extend from source 16 along a beam plane 24. Beam plane 24, generally referred to as the "fan beam plane", contains the centerline of focal spot 18 and the centerline of beam 20 of each source 16. Each x-ray beam 20 is collimated by a collimator (not shown) to lie within in an X-Y plane of a Cartesian coordinate system and generally referred to as an "imaging plane". Each detector array 22 is formed by an array of detector elements 26 which together sense the projected x-rays that pass through a medical patient 28. Detector array 22 may be a single slice detector or a multislice detector. Each detector element 26 produces an electrical signal that represents the intensity of an impinging x-ray beam and hence the attenuation of the beam as it passes through patient 28. During a scan to acquire x-ray projection data, gantry 12 and the components mounted thereon rotate about a center of rotation, or iso-center, 30.

Rotation of gantry 12 and the operation of each x-ray source 16 are governed by a control mechanism 34 of CT system 10. Control mechanism 34 includes an x-ray controller 36 that provides power and timing signals to each x-ray source 16 and a gantry motor controller 38 that controls the rotational speed and position of gantry 12. More specifically, altering the signals supplied to x-ray controller 36 determines when and for how long x-ray beam 20 is emitted from each x-ray source 16. Similarly, the rotational speed of gantry 12 is determined, or altered, by supplying the appropriate signals to gantry motor controller 38. A data acquisition system (DAS) 40 in control mechanism 34 samples analog data from detector elements 26 and converts the data to digital signals for subsequent processing. A sampling rate of DAS 40 is adjustable, or variable, so that the rate at which the data supplied from elements 26 may be increased or decreased. An image reconstructor 42 receives sampled and digitized x-ray data from DAS 40 and performs high speed image reconstruction. The reconstructed image is applied as an input to a computer 44 which stores the image in a mass storage device 46.

Computer 44 also receives commands and scanning parameters from an operator via console 48 that has a keyboard. An associated cathode ray tube display 50 allows the operator to observe the reconstructed image and other data from computer 44. The operator supplied commands and parameters are used by computer 44 to provide control signals and information to DAS 40, x-ray controller 36 and gantry motor controller 38. In addition, computer 44 operates a table motor controller 52 which controls a motorized table 54 to position patient 28 in gantry 12. Particularly, table 54 moves portions of patient 28 through a gantry opening 56.

In one embodiment, system 10 includes a synchronization unit, or circuit 100 to identify or determine, a physiological cycle of the object, i.e., a heart. More specifically and in one embodiment, circuit 100 is coupled to computer 44 and generates a physiological cycle signal representative of the heart including a plurality of phases of the object, e.g., a systole and a diastole phases. System 10 utilizes the physiological signal to synchronize the timing of the emission of x-ray beam 16, the collection rate of projection data segments using DAS 40, and the rotational speed of gantry 12 so that an image of the heart is generated for the determined, or selected, phase of a heart cycle.

Figure 3:
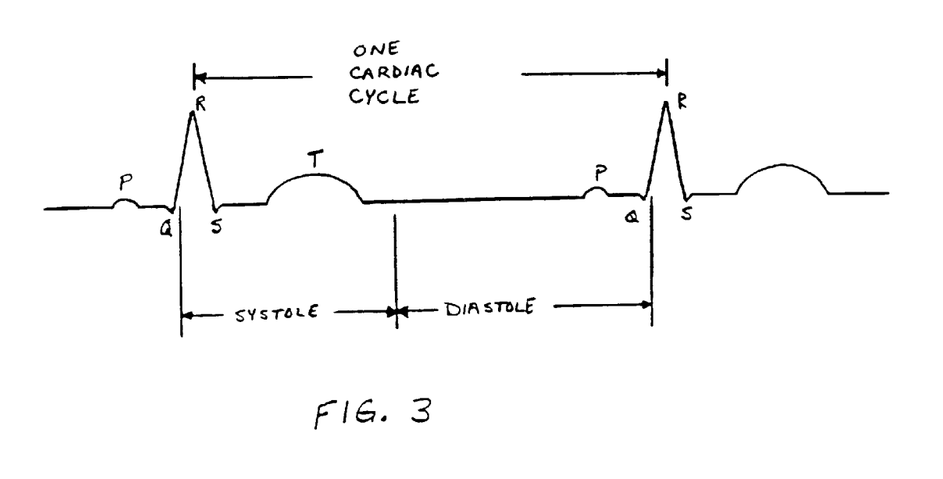
FIG. 3 is a illustration of a physiological cycle of a heart.

More specifically and in one embodiment, circuit 100 measures, or detects, the electrical activity of the heart of patient 28 to identify or determine the cardiac phase signal for each cycle of a patient's heart. In one embodiment, an output signal of at least one electrode (not shown) attached to patient 28 is supplied to an electronic amplifier (not shown) within circuit 100 which generates the cardiac phase signal. For example, and as shown in FIG. 3, the cardiac cycle signal waveform illustrates one cardiac cycle including the systole condition, or phase, and a diastole condition or phase, of the heart. The portion of the signal which is labeled Q, R and S is referred to as the QRS complex, in which the R-feature, or R-wave, is the most prominent, highest amplitude, feature of the entire signal. In one embodiment, the cardiac cycle determines the period of each heart cycle and the timing of each phase of the heart. The amount of time required for the heart to complete one cardiac cycle is identified as a cardiac period, w, and typically is defined as beginning with a R-wave and continuing until the occurrence of the next R-wave. In other embodiments, the cardiac cycle signal may be generated by an EKG subsystem or heart monitoring device as known in the art.

In one embodiment, system 10 is configured to generate a volumetric image of an entire object within patient 28, for example a heart (not shown), by collecting at least one portion, or segment, of a projection data set during each rotation of gantry 12. After collecting the entire projection data set, the projection data segments are combined and a reconstruction algorithm is used to generate the volumetric tomographic image of the heart. More specifically and in one embodiment, each segment of projection data is collected for a determined time period, or temporal window for a pre-determined, or operator selected, phase of the heart during rotation of gantry 12. After completing a plurality rotations of each x-ray source 16, a reconstruction algorithm stored within image reconstructor 42 combines the projection data segments and generates a volumetric cross-sectional image of the heart for the determined phase.

More specifically and in one embodiment, system 10 utilizes circuit 100 to identify the physiological cycle of the object, i.e., a heart and a plurality of phases of the heart. An operator then selects at least one phase of the heart to image using the physiological signal. For example, the operator utilizes console 48 to select a systole phase of the heart. For each selected phase of the object, at least one segment of projection data is collected during each rotation of each x-ray source 16.

More specifically, each segment of projection data, in one embodiment, is generated, or collected, by emitting an x-ray beam 20 toward an x-ray detector array 22 for a determined imaging temporal period, $R_1$, during each selected phase. Particularly, during each rotation of each x-ray source 16, an x-ray beam 20 is emitted for the determined imaging temporal period. The projection data collected via each detector array 22 during the temporal period represents a range of angular positions. Specifically, utilizing the cycle signal supplied from circuit 100, the emission of x-ray beam 16 is limited to the nominal period of Rt at the defined phase of each cycle. More specifically, utilizing the physiological cycle signal, the emission of x-ray beam 16 is turned on and off by altering a signal supplied to x-ray controller 36. In one embodiment, the imaging temporal period is in a range of 10 mS to 50 mS.

The projection data segment acquired from detector array 22 during the emission of x-ray beam 20 represents a small, or limited, portion of angular positions within the time duration of Rt. Particularly, the cycle signal is utilized by DAS 40 to alter the sampling rate of each detector array 22 so that the outputs of elements 26 are sampled only during the period of emission of x-ray beam 20. During each subsequent rotation of each x-ray source 16, a segment of projection data is collected for a different radial, or projection, angle for each selected phase.

In one embodiment, a rotational speed of each x-ray source 16 is altered, or determined, so that at least one segment of projection data is collected during each rotation of each x-ray source 16. More specifically and in one embodiment, the rotational speed of each x-ray source 16 is altered so that each segment of projection data for each selected phase of the object is collected from a different projection angle, or range of projection angles. In one embodiment, by altering the signals supplied to gantry motor controller 38, each x-ray source 16 is rotated a plurality of rotations so that projection data is collected for a projection angle range of (180 degrees plus a fan angle). For example, segments of projection data for each selected phase of the heart are collected from a projection angle range of 225 degrees. As a result of each segment representing an approximate 18 degree change in projection angle, a complete set of projection data may be acquired in about 13 to 20 seconds, less than a single breath-holding time, depending upon the imaging requirements.

More particularly and in one embodiment, the rotational speed of each x-ray source 16, in rotations per second, is determined in accordance with:

$$V_G = \frac{1}{(T_c \pm (n * R_t))}$$

where:

Tc is the cardiac cycle time in seconds;

n is an integer constant; and

Rt is the determined imaging temporal period in seconds.

For example, if n equals one, Tc equals 1 second and Rt equals 0.05 seconds, the rotating speed of each x-ray source 16 is approximately 1.05 revolutions per second or 0.95 revolutions per second. As a result, a complete set of projection data segments is collected in 13 to 20 seconds depending on image quality requirements.

In one embodiment, the time required to collect a complete set of projection data may be reduced by altering the rotational speed of each x-ray source 16 in accordance with:

$$V_G = \left(\frac{180 + \frac{y}{n}}{180 * w}\right)$$

(in rotations per second)
where:

w is the period of a physiological cycle (in seconds),

γ is the projection angle range for a complete projection data set (in degrees), and n is a selected integer number of cycles to collect a complete projection data set.

In an alternative embodiment, the time required to collect a complete set of projection data may be reduced by altering the rotational speed of each x-ray source 16 in accordance with:

$$V_G = \left(\frac{360 + \frac{y}{n}}{360 * w}\right)$$

(in rotations per second)
where:

w is the period of a physiological cycle (in seconds),

γ is the projection angle range for a complete projection data set (in degrees), and n is a selected integer number of cycles to collect a complete projection data set.

Using this method of altering the rotational speed of each x-ray source 16, the data span within each physiological cycle is improved from ($\gamma/(360*V_G)$) seconds to ($\gamma/(360*V_G*n)$) seconds, and improvement of a factor of n. For example, utilizing this method in a single slice CINE CT mode, a projection data set representing one slice of projection data is collected in (n*t) seconds. The rotation speed of each x-ray source 16 may also be altered in accordance with this method in a Helical mode to obtain projection data to generate a volumetric data in one scan of the object.

More specifically and in one embodiment, in a multi-slice helical CT scan mode, projection data is collected using a relatively fast table speed. Using multiple rows of each detector array 22, fast volume coverage is achieved. Particularly, z resolution degradation is minimized when the speed of table 54, as determined by table controller 52, is altered so that the table speed, s, is determined in accordance with:

$(i*d)/w,$ where, d is a detector row spacing of detector array 22, and i is an integer.

For example, where d equals 5 mm, w equals 0.8 seconds and i equals 3, the z resolution degradation is minimized when the speed of table 54 is 18.95 mm/second.

In one embodiment, after collecting the segments of projection data, the segments are combined into a projection data set and a cross-sectional image of the object is generated from the projection data set. More specifically, a projection data set is generated for each selected phase of the object by combining the projection data segments collected for the selected phase. For example, where a first selected phase is a systole phase of the heart, a first projection data set is generated by combining the projection data segments collected from the plurality of projection angles for the systole phase of the heart. In a similar manner, a separate projection data set is then generated for each additional selected phase of the object. For example, a second projection data set may be generated by combining the projection data segments collected from the diastole phase of the heart.

In one embodiment, the projection data set generated for a selected phase is utilized to generate a cross-sectional image of the entire object. More specifically and in one embodiment, a cross-sectional, or volumetric tomographic, image is generated, using a reconstruction algorithm stored in image reconstructor 42, for each selected phase of the object. Each projection data set is used to generate a separate cross-sectional image of the entire object for each selected phase of the object. For example, using system 10 in a single cardiac phase mode, where the operator selects only a first phase to generate an image, the first set of projection data is used to generate a cross-sectional image of the entire heart in the first phase.

In one embodiment, circuit 100 also monitors each physiological cycle to determine if an arrhythmic, or abnormal, condition exists to determine whether the segments of projection collected are valid. More specifically and in one embodiment, circuit 100 determines an average cycle period by measuring the time period of a selected number of cycles. For each completed cycle of the object, circuit 100 compares the average cycle period to a cycle period for the completed cycle. If the completed cycle period exceeds the average cycle period plus or minus a tolerance, the completed cycle is identified as an arrhythmic cycle. The arrhythmic cycle causes the collected segments of projection data to not represent the selected phase. In one embodiment, the segments collected during the arrhythmic cycle are not used and replacement segments of projection data are collected.

In an alternative embodiment defined as a multi-phase cardiac mode, projection data sets are generated from a plurality of selected phases of the object during each rotation of each x-ray source 16. More specifically, segments of projection data are collected as described above except that each x-ray source 16 is turned on a plurality of times during each rotation so that segments of projection data are collected from plurality of selected phases of the object during each rotation. In another embodiment of the multi-phase cardiac mode, segments of projection data are collected from a plurality of segments for each selected phase of the object during each rotation of each x-ray source 16.

In the multi-phase cardiac imaging mode, projection data is collected for a plurality of selected cardiac phases during each rotation of gantry 12 so that separate images are generated for each selected cardiac phase. More specifically and in one embodiment, the multi-phase cardiac imaging mode operates similar to the single phase cardiac imaging mode except separate images are generated for a plurality of phases of the heart. Initially, the user determines, or selects, a plurality of cardiac phases to be imaged. By altering the amount of time between each selected phase, images of different phases of the heart may be generated, for example for a systolic and a diastolic phase. After selecting a plurality of phases, gantry 12 is rotated as described above. For each rotation of gantry 12, x-ray beam 20 is emitted from source 14 toward detector array 22 for each selected cardiac phase and a segment of projection data is collected by detector array 22 for each selected cardiac phase. Particularly and as described above, utilizing circuit 100, the rotational speed of gantry 12 and the sampling rate of DAS 40 are altered so that projection data is collected for the plurality of cardiac phases. After collecting a complete set of projection for each cardiac phase as described above, the reconstruction algorithm generates a volumetric image of each selected phase of the heart.

Utilizing the above described mode and by increasing the rotational speed of gantry 12, either the image temporal resolution or the total scan time for a given organ coverage is significantly improved. For example, if gantry 12 is rotated so that gantry 12 completes two complete rotation during a single cardiac cycle, the temporal resolution is improved by 50% versus a system completing one rotation per cardiac cycle.

In yet another embodiment of the present invention, an image of cardiac wall motion may be generated by acquiring multiple segments of projection data during a short period of time, for example four seconds. In an alternative embodiment, continuous segments of projection data is collected and the data is rebinned for different phases of a cardiac cycle.

The above described imaging system generates images of a moving object by gathering segments of projection data for a selected phase of the object so that motion artifacts are minimized. In addition, the imaging system generates cross-sectional images of the entire object for each selected phase of the object.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, imaging system may be configured as a "fourth generation" system having at least one rotating x-ray source and at least one fixed position detector array. Accordingly, the spirit and scope of the invention are to be limited only by the terms of the appended claims.

Figure 4:
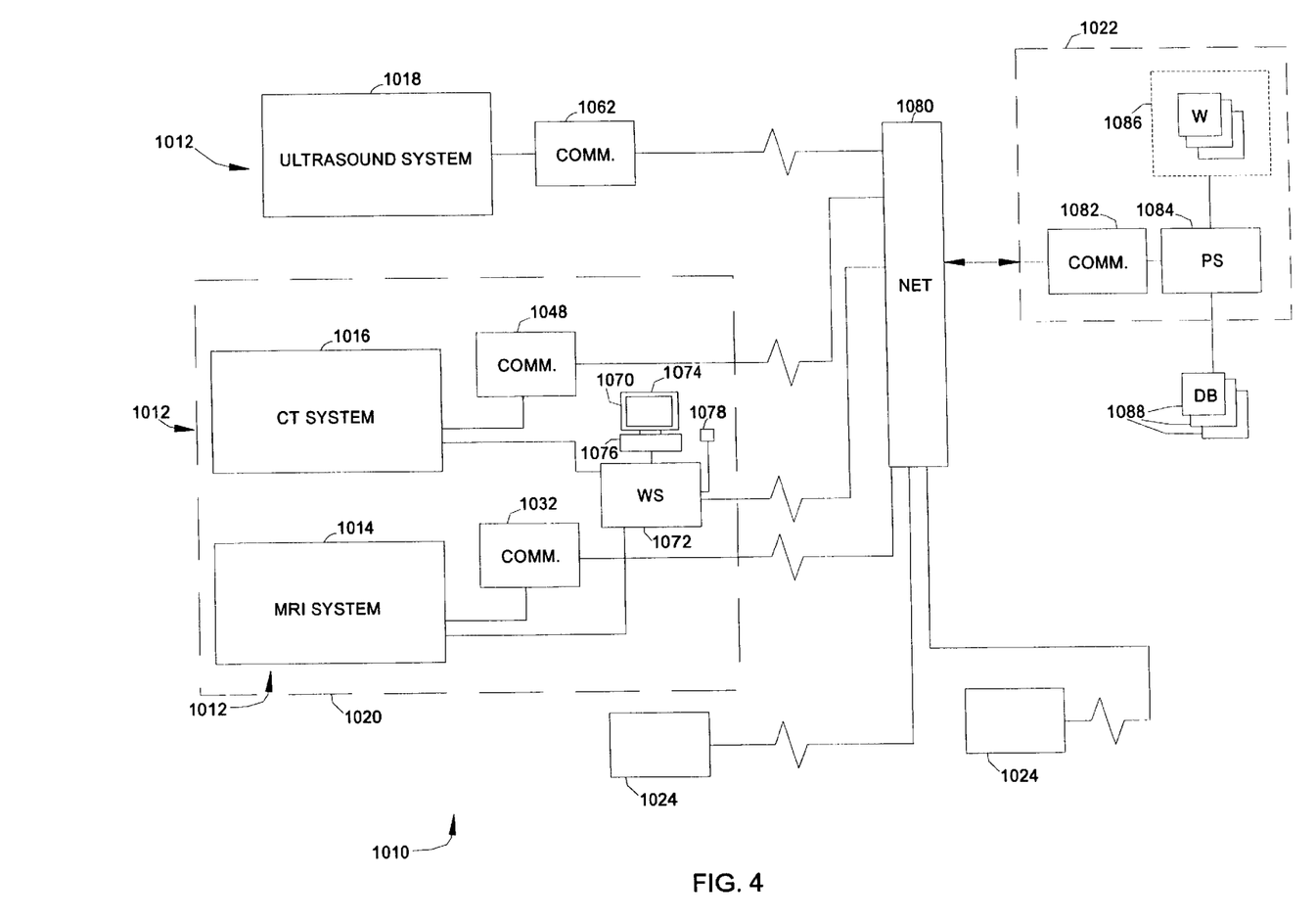
FIG. 4 is a diagrammatical representation of a series of medical diagnostic systems coupled to a service facility via a network connection for providing remote services and data interchange between the diagnostic systems and the service facility.

Referring now to FIG. 4, a service system 1010 is illustrated for providing remote service to a plurality of medical diagnostic systems 1012, including systems such as imaging system 10 described with reference to FIG. 1. In the embodiment illustrated in FIG. 4, the medical diagnostic systems include a magnetic resonance imaging (MRI) system 1014, a computed tomography (CT) system 1016, and an ultrasound imaging system 1018. The diagnostic systems may be positioned in a single location or facility, such as a medical facility 1020, or may be remote from one another as shown in the case of ultrasound system 1018. The diagnostic systems are serviced from a centralized service facility 1022. Moreover, a plurality of field service units 1024 may be coupled in the service system for transmitting service requests, verifying service status, transmitting service data and so forth as described more fully below.

In the exemplary embodiment of FIG. 4, several different system modalities are provided with remote service by the service facility. Remote services include but are not limited to services, such as, remote monitoring, remote system control, immediate file access from remote locations, remote file storage and archiving, remote resource pooling, remote recording, and remote high speed computations. Remote services are provided to a particular modality depending upon the capabilities of the service facility, the types of diagnostic systems subscribing to service contracts with the facility, as well as other factors.

Depending upon the modality of the systems, various subcomponents or subsystems will be included. In the case of MRI system 1014, such systems will generally include a scanner, a control and signal detection circuit, a system controller, and an operator station. MRI system 1014 includes a uniform platform for interactively exchanging service requests, messages and data with service facility 1022 as described more fully below. MRI system 1014 is linked to a communications module 1032, which may be included in a single or separate physical package from MRI system 1014. In a typical system, additional components may be included in system 1014, such as a printer or photographic system for producing reconstructed images based upon data collected from the canner.

Similarly, CT system 1016 will typically include a scanner, a signal acquisition unit, and a system controller. The scanner detects portions of x-ray radiation directed through a subject of interest. The controller includes circuitry or commanding operation of the scanner and for processing and reconstructing image data based upon the acquired signals. CT system 1016 is linked to a communications module 1048 for transmitting and receiving data for remote services. Moreover, like MRI system 1014, CT system 1016 will generally include a printer or similar device for outputting reconstructed images based upon data collected by the scanner.

In the case of ultrasound system 1018, such systems will generally include a scanner and data processing unit and a system controller. Ultrasound system 1018 is coupled to a communications module 1062 for transmitting service requests, messages and data between ultrasound system 1018 and service facility 1022.

Although reference is made herein generally to "scanners" in diagnostic systems, that term should be understood to include medical diagnostic data acquisition equipment generally, not limited to image data acquisition, as well as to picture archiving communications and retrieval systems, image management systems, facility or institution management systems, viewing systems and the like, in the field of medical diagnostics.

Where more than one medical diagnostic system is provided in a single facility or location, as indicated in the case of MRI and CT systems 1014 and 1016 in FIG. 4, these may be coupled to a management station 1070, such as in a radiology department of a hospital or clinic. The management station may be linked directly to controllers for the various diagnostic systems. The management system may include a computer workstation or personal computer 1072 coupled to the system controllers in an intranet configuration, in a file sharing configuration, a client/server arrangement, or in any other suitable manner. Moreover, management station 1070 will typically include a monitor 1074 for viewing system operational parameters, analyzing system utilization, and exchanging service requests and data between the facility 1020 and the service facility 1022. Input devices, such as a standard computer keyboard 1076 and mouse 1078, may also be provided to facilitate the user interface.

It should be noted that, alternatively, the management system, or other diagnostic system components, may be "stand-alone" or not coupled directly to a diagnostic system. In such cases, the service platform described herein, and some or all of the service functionality nevertheless be provided on the management system. Similarly, in certain applications, a diagnostic system may consist of a stand-alone or networked picture archiving communications and retrieval system or a viewing station provided with some or all of the functionality described herein.

The communication modules mentioned above, as well as workstation 1072 and field service units 1024 may be linked to service facility 1022 via a remote access network 1080. For this purpose, any suitable network connection may be employed. Presently preferred network configurations include both proprietary or dedicated networks, as well as open networks, such as the Internet. Data may be exchanged between the diagnostic systems, field service units, and remote service facility 1022 in any suitable format, such as in accordance with the Internet Protocol (IP), the Transmission Control Protocol (TCP), or other known protocols. Moreover, certain of the data may be transmitted or formatted via markup languages such as the HyperText Markup Language (HTML), or other standard languages. The presently preferred interface structures and communications components are described in greater detail below.

Within service facility 1022, messages, service requests and data are received by communication components as indicated generally at reference numeral 1082. Components 1082 transmit the service data to a service center processing system, represented generally at reference numeral 1084 in FIG. 4. The processing system manages the receipt, handling and transmission of service data to and from the service facility. In general, processing system 1084 may include one or a plurality of computers, as well as dedicated hardware or software servers for processing the various service requests and for. receiving and transmitting the service data as described more fully below.

Service facility 1022 also includes a bank of operator workstations 1086 which may be staffed by personnel who address the service requests and provide off and on-line service to the diagnostic systems in response to the service requests. Also, processing system 1084 may be linked to a system of databases or other processing systems 1088 at or remote from the service facility 1022. Such databases and processing systems may include extensive database information on operating parameters, service histories, and so forth, both for particular subscribing scanners, as well as for extended populations of diagnostic equipment.

Figure 5:
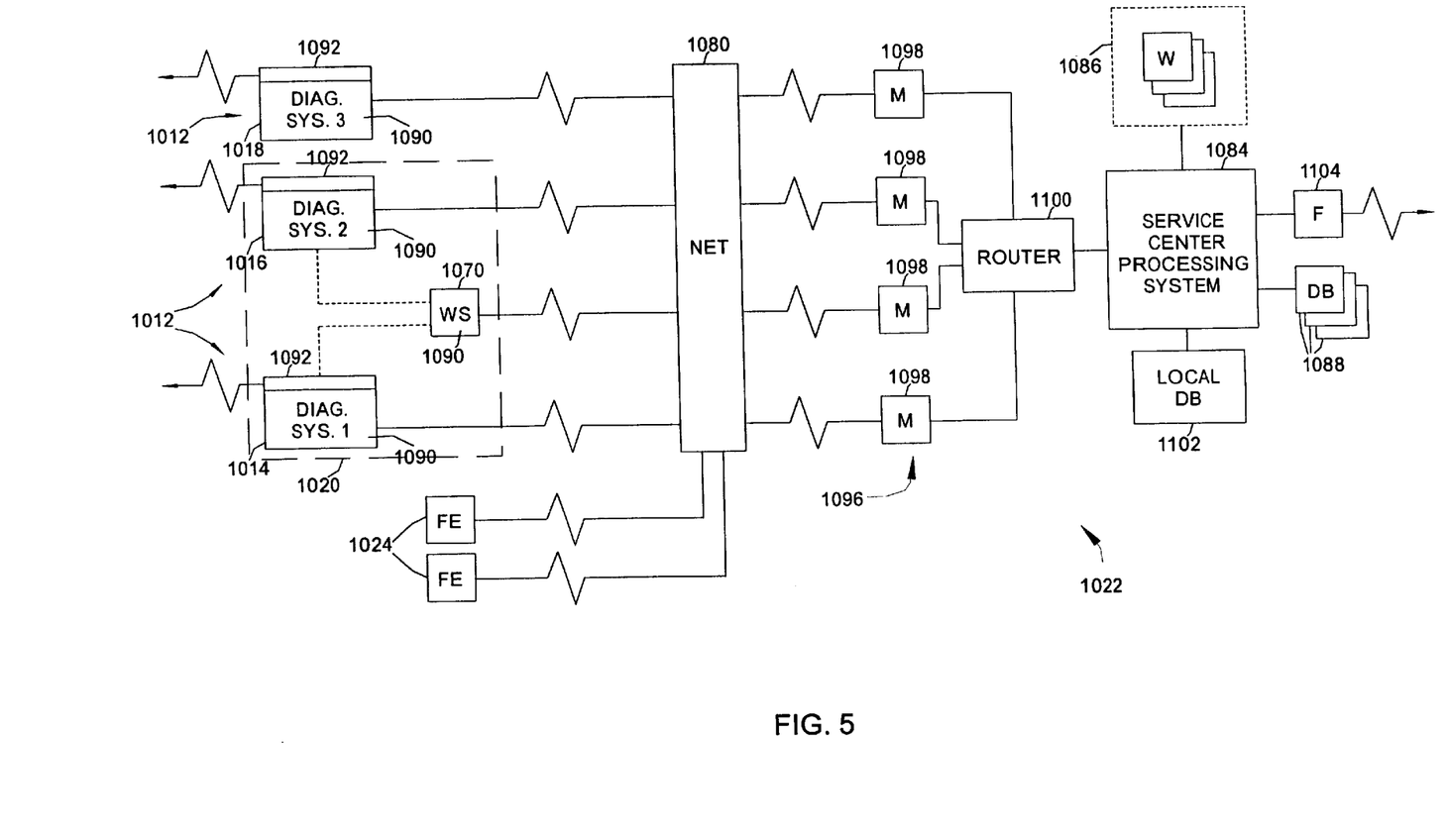
FIG. 5 is a block diagram of the systems shown in FIG. 4 illustrating certain functional components of the diagnostic systems and the service facility.

FIG. 5 is a block diagram illustrating the foregoing system components in a functional view. As shown in FIG. 5, the field service units 1024 and the diagnostic systems 1012 can be linked to the service facility 1022 via a network connection as illustrated generally at reference numeral 1080. Within each diagnostic system 1012, a uniform service platform 1090 is provided.

Platform 1090, which is described in greater detail below with particular reference to FIG. 6, includes hardware, firmware, and software components adapted for composing service requests, transmitting and receiving service data, establishing network connections and managing financial or subscriber arrangements between diagnostic systems and the service facility. Moreover, the platforms provide a uniform graphical user interface at each diagnostic system, which can be adapted to various system modalities to facilitate interaction of clinicians and radiologists with the various diagnostic systems for service functions. The platforms enable the scanner designer to interface directly with the control circuitry of the individual scanners, as well as with memory devices at the scanners, to access image, log and similar files needed for rendering requested or subscribed services. Where a management station 1070 is provided, a similar uniform platform is preferably loaded on the management station to facilitate direct interfacing between the management station and the service facility. In addition to the uniform service platform 1090, each diagnostic system is preferably provided with an alternative communications module 1092, such as a facsimile transmission module for sending and receiving facsimile messages between the scanner and remote service facilities.

Messages and data transmitted between the diagnostic systems and the service facility traverse a security barrier or "firewall" contained within processing system 1084 as discussed below, which prevents unauthorized access to the service facility in a manner generally known in the art. A modem rack 1096, including a series of modems 1098, receives the incoming data, and transmits outgoing data through a router 1100 which manages data traffic between the modems and the service center processing system 1084.

In the diagram of FIG. 5, operator workstations 1086 are coupled to the processing system, as are remote databases or computers 1088. In addition, at least one local service database 1102 is provided for verifying license and contract arrangements, storing service record files, log files, and so forth. Moreover, one or more communication modules 1104 are linked to processing system 1084 to send and receive facsimile transmissions between the service facility and the diagnostic systems or field service units.

Figure 6:
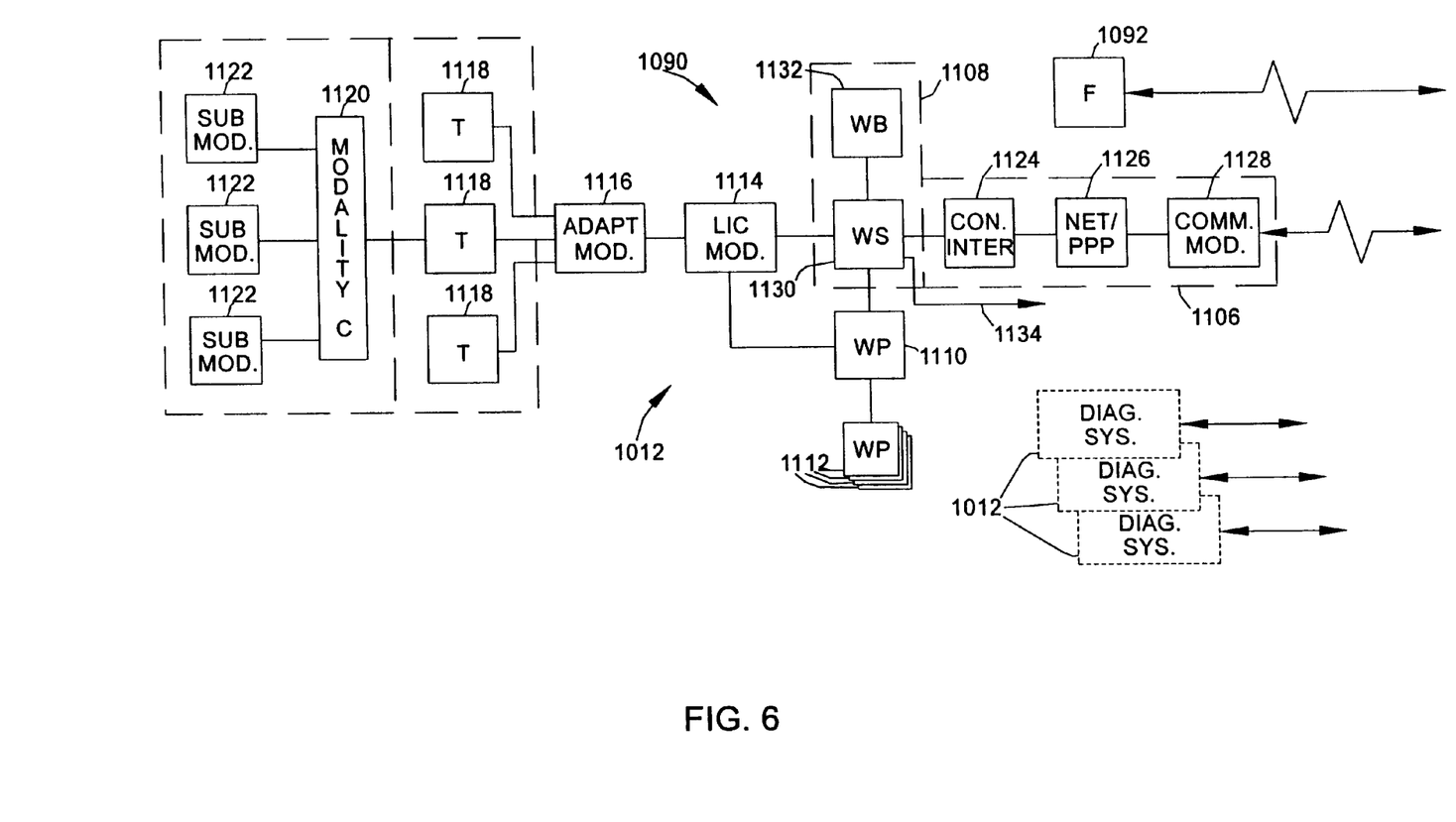
FIG. 6 is a block diagram of certain functional components within a diagnostic system of the type shown in FIG. 4 and FIG. 5 for facilitating interactive remote servicing of the diagnostic system.

FIG. 6 illustrates diagrammatically the various functional components comprising the uniform service platform 1090 within each diagnostic system 1012. As shown in FIG. 6, the uniform platform includes a device connectivity module 1106, as well as a network connectivity module 1108. Network connectivity module 1108 accesses a main web page 1110 which, as mentioned above, is preferably a markup language page, such as an HTML page displayed for the system user on a monitor at the diagnostic system. Main web page 1110 is preferably accessible from a normal operating page in which the user will conFig. examination requests, view the results of examinations, and so forth such as via an on-screen icon. Through main web page 1110, a series of additional web pages 1112 are accessible. Such web pages permit remote service requests to be composed and transmitted to the remote service facility, and facilitate the exchange of other messages, reports, software, protocols, and so forth as described more fully below.

It should be noted that as used herein the term "page" includes a user interface screen or similar arrangement which can be viewed by a user of the diagnostic system, such as screens providing graphical or textual representations of data, messages, reports and so forth. Moreover, such pages may be defined by a markup language or a programming language such as Java, per, java script, or any other suitable language.

Network connectivity module 1108 is coupled to a license module 1114 for verifying the status of license, fee or contractual subscriptions between the diagnostic system and the service facility. As used herein, the term "subscription" should be understood to include various arrangements, contractual, commercial or otherwise for the provision of services, information, software, and the like, both accompanies with or without payment of a fee. Moreover, the particular arrangements manages by systems as described below may include several different types of subscriptions, including time-expiring arrangements, one-time fee arrangements, and so-called "pay per use" arrangements, to mention but a few.

License module 1114 is, in turn, coupled to one or more adapter utilities 1116 for interfacing the browser, server, and communications components with modality interface tools 1118. In a presently preferred configuration, several such interface tools are provided for exchanging data between the system scanner and the service platform. For example, modality interface tools 1118 may include applets or servlets for building modality-specific applications, as well as configuration templates, graphical user interface customization code, and so forth. Adapters 1116 may interact with such components, or directly with a modality controller 1120 which is coupled to modality-specific subcomponents 1122.

The modality controller 1120 and modality-specific subcomponents 1122 will typically include a reconfigured processor or computer for executing examinations, and memory circuitry for storing image data files, log files, error files, and so forth. Adapter 1116 may interface with such circuitry to convert the stored data to and from desired protocols, such as between the HyperText Transfer Protocol (HTTP) and DICOM, a medical imaging standard for data presentation. Moreover, transfer of files and data as described below may be performed via any suitable protocol, such as a file transfer protocol (FTP) or other network protocol.

In the illustrated embodiment, device connectivity module 1106 includes several components for providing data exchange between the diagnostic system and the remote service facility. In particular, a connectivity service module 1124 provides for interfacing with network connectivity module 1108. A Point-to-Point Protocol (PPP) module 1126 is also provided for transmitting Internet Protocol (IP) packets over remote communication connections. Finally, a modem 1128 is provided for receiving and transmitting data between the diagnostic system and the remote service facility. As will be appreciated by those skilled in the art, various other network protocols and components may be employed within device connectivity module 1106 for facilitating such data exchange.

Network connectivity module 1108 preferably includes a server 1130 and a browser 1132. Server 1130 facilitates data exchange between the diagnostic system and the service facility, and permits a series of web pages 1110 and 1112 to be viewed via browser 1132. In a presently preferred embodiment, server 1130 and browser 1132 support HTTP applications and the browser supports java applications. Other servers and browsers, or similar software packages may, of course, be employed for exchanging data, service requests, messages, and software between the diagnostic system, the operator and the remote service facility. Finally, a direct network connection 1134 may be provided between server 1130 and an operator workstation, such as management station 1070 within the medical facility (see FIGS. 4 and 5).

In a present embodiment, the components comprising network connectivity module may be configured via an application stored as part of the uniform platform. In particular, a Java application licensed to a service engineer enables the engineer to configure the device connectivity at the diagnostic system to permit it to connect with the service facility.

Figure 7:
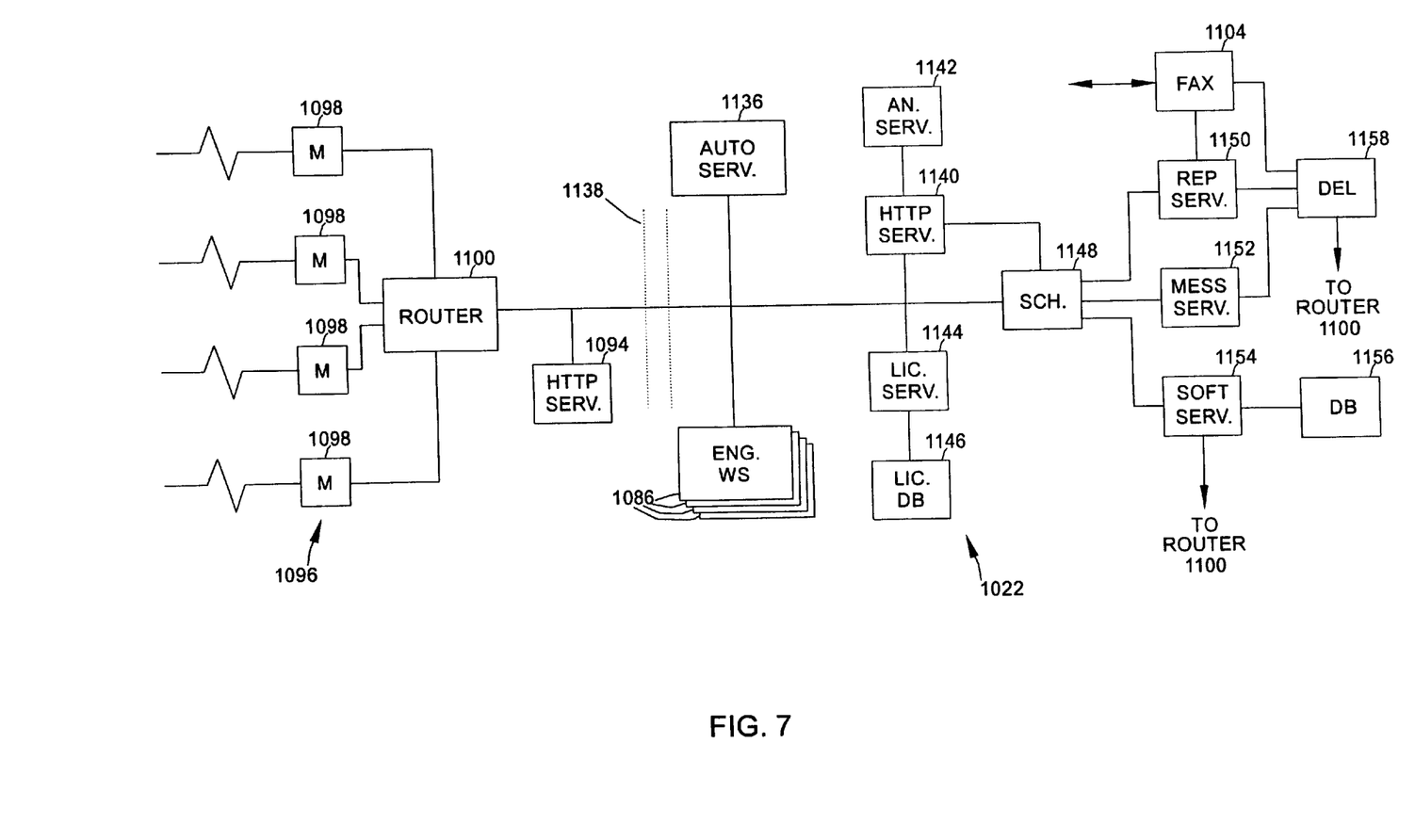
FIG. 7 is a block diagram of certain of the functional components of the service facility illustrated in FIG. 4 and FIG. 5 for rendering interactive remote service to a plurality of medical diagnostic systems.

FIG. 7 illustrates exemplary functional components for service facility 1022. As indicated above, service facility 1022 includes a modem rack 1096 comprising a plurality of modems 1098 coupled to a router 1100 for coordinating data communications with the service facility. An HTTP service server 1094 receives and directs incoming and outgoing transactions with the facility. Server 1094 is coupled to the other components of the facility through a firewall 1138 for system security. Operator workstations 1086 are coupled to the port manager for handling service requests and transmitting messages and reports in response to such requests.

An automated service unit 1136 may also be included in the service facility for automatically responding to certain service requests, sweeping subscribing diagnostic systems for operational parameter data, and so forth, as described below. In a presently preferred embodiment, the automated service unit may operate independently of or in conjunction with the interactive service components comprising processing system 1084. It should be noted that other network or communications schemes may be provided for enabling the service facility to communicate and exchange data and messages with diagnostic systems and remote service units, such as systems including outside Internet service providers (ISP's), virtual private networks (VPN's) and so forth.

Behind firewall 1138, an HTTP application server 1140 coordinates handling of service requests, messaging, reporting, software transfers and so forth. Other servers may be coupled to HTTP server 1140, such as service analysis servers 1142 configured to address specific types of service requests, as described more fully below. In the illustrated embodiment, processing system 1084 also includes a license server 1144 which is coupled to a license database 1146 for storing, updating and verifying the status of diagnostic system service subscriptions. Alternatively, w here desired, license server 1144 may be placed outside of fire wall 1138 to verify subscription status prior to admission to the service facility.

Handling of service requests, messaging, and reporting is further coordinated by a scheduler module 1148 coupled to HTTP server 1140. Scheduler module 1148 coordinates activities of other servers comprising the processing system, such as a report server 1150, a message server 1152, and a software download server 1154. As will be appreciated by those skilled in the art, servers 1150, 1152 and 1154 are coupled to memory devices (not shown) for storing data such as addresses, log files, message and report files, applications software, and so forth. In particular, as illustrated in FIG. 7, software server 1154 is coupled via one or more data channels to a storage device 1156 for containing transmittable software packages which may be sent directly to the diagnostic systems, accessed by the diagnostic systems, or supplied on pay-per-use or purchase basis. Message and report servers 1152 and 1150 are further coupled, along with communications module 1104, to a delivery handling module 1158, which is configured to receive outgoing messages, insure proper connectivity with diagnostic systems, and coordinate transmission of the messages.

In a presently preferred embodiment, the foregoing functional circuitry may be configured as hardware, firmware, or software on any appropriate computer platform. For example, the functional circuitry of the diagnostic systems may be programmed as appropriate code in a personnel computer or workstation either incorporated entirely in or added to the system scanner. The functional circuitry of the service facility may include additional personal computers or workstations, in addition to a main frame computer in which one or more of the servers, the scheduler, and so forth, are configured. Finally, the field service units may comprise personal computers or laptop computers of any suitable processor platform. It should also be noted that the foregoing functional circuitry may be adapted in a variety of manners for executing the functions described herein. In general, the functional circuitry facilitates the exchange of remote service data between the diagnostic systems and a remote service facility, which is preferably implemented in an interactive manner to provide regular updates to the diagnostic systems of service activities.

As described above, both the diagnostic systems and the field service units preferably facilitate interfacing between a variety of diagnostic system modalities and the remote service facility via a series of interactive user-viewable pages. Exemplary pages include capabilities of providing interactive information, composing service requests, selecting and transferring messages, reports and diagnostic system software, and so forth. Pages facilitate the interaction and use of remote services, such as, remote monitoring, remote system control, immediate file access from remote locations, remote file storage and archiving, remote resource pooling, remote recording, and remote high speed computations.

The user can access specific documents described in text areas of the pages by selection of all or a portion of the text describing the documents. In the presently preferred embodiment, the accessed documents may be stored in local memory devices within the diagnostic system, or selection of the text may result in loading of a uniform resource locator (URL) for accessing a remote computer or server via a network link.

Advantageously, service system 1010 (FIG. 4) provides remote services, such as, remote upgrades, remote diagnostics, remote servicing, remote viewing, remote file storage, remote control, and remote adjustments to system parameters and functions. Furthermore, remote services may provide for contractual arrangements, such as, per use licenses which lease the medical diagnostic equipment based on use. Additionally, remote services may also include expert on-line assistance for image scanning techniques, image analysis, pathology detection, imaging unit maintenance, and other expert-aided operations.

While the embodiments illustrated in the Figs. and described above are presently preferred, it should be understood that the embodiments are offered by way of example only. Other embodiments may include enhanced remote features made possible by the network structures and functionalities described herein. The invention is not limited to a particular embodiment, but extends to various modifications, combinations, and permutations that nevertheless fall within the scope and spirit of the appended claims.

What is claimed is:

1. A method for generating an image of an object using a computed tomography (CT) imaging system, the imaging system including at least one x-ray detector array and at least one rotating x-ray source projecting an x-ray beam, the method comprising the steps of:

identifying a physiological cycle of the object, the cycle comprising a plurality of phases;

selecting at least one phase of the object;

collecting at least one segment of projection data for each selected phase of the object during each rotation of each x-ray source;

generating a projection data set by combining the projection data segments;

generating a cross-sectional image of the entire object from the projection data set; and communicating the image or data associated with the image to a remote facility, the remote facility providing remote services over a network.

2. A method in accordance with claim 1 wherein generating a projection data set by combining the projection data segments comprises the step of generating a projection data set for each selected phase of the object by combining the projection data segments collected for the selected phase.

3. A method in accordance with claim 1 wherein collecting at least one segment of projection data for each selected phase of the object during each rotation of each x-ray source comprises the steps of:

rotating each x-ray source a plurality of rotations; and emitting an x-ray beam from each x-ray source toward each x-ray detector array from a plurality of projection angles.

4. A method in accordance with claim 3 wherein collecting at least one segment of projection data for each selected phase of the object during each rotation of each x-ray source further comprises the step of collecting each segment of projection data for the selected phase from a different projection angle.

5. A method in accordance with claim 4 wherein collecting each segment of projection data for the selected phase from a different projection angle comprises the step of altering a rotational speed of each x-ray source.

6. A method in accordance with claim 5 wherein emitting an x-ray beam from each x-ray source toward each x-ray detector array from plurality of projection angles comprises the step of emitting an x-ray beam from each x-ray source for a determined imaging temporal period.

7. A method in accordance with claim 6 wherein the rotational speed of each x-ray source is determined in accordance with:

$$V_G = \frac{1}{(T_c \pm (n * R_t))}$$

where:

Tc is the cardiac cycle time in seconds;

n is an integer constant; and

Rt is the determined imaging temporal period in seconds.

8. A method in accordance with claim 6 wherein collecting at least one segment of projection data for each cycle of the object comprise the step of altering the rotational speed of each x-ray source in accordance with:

$$V_G = \left(\frac{180 + \frac{y}{n}}{180 * w}\right)$$

(in rotations per second)

where:

w is a period of a physiological cycle (in seconds),

γ is a projection angle range for a complete projection data set (in degrees), and n is a selected integer number of cycles to collect a complete projection data set.

9. A method in accordance with claim 6 wherein collecting at least one segment of projection data for each cycle of the object comprise the step of altering the rotational speed of each x-ray source in accordance with:

$$V_G = \left(\frac{360 + \frac{y}{n}}{360 * w}\right)$$

(in rotations per second)

where:

w is a period of a physiological cycle (in seconds),

γ is a projection angle range for a complete projection data set (in degrees), and n is a selected number of cycles to collect a complete projection data set.

10. A method in accordance with claim 1 wherein the imaging system includes a first x-ray source, a second x-ray source, a first detector array and a second detector array.

11. A method in accordance with claim 1 wherein selecting at least one phase of the object comprises the steps of:

selecting a first selected phase of the object; and selecting a second selected phase of the object.

12. A method in accordance with claim 1 wherein identifying a physiological cycle of the object comprises the step of identifying a physiological cycle of a heart including a systolic phase and a diastolic phase.

13. A method in accordance with claim 1 wherein identifying a physiological cycle of the object comprises the step of identifying a physiological cycle of a respiratory system.

14. A method in accordance with claim 1 wherein generating a projection data set by combining the projection data segments comprises the steps of:

rotating each x-ray source a plurality of projection angles;

collecting projection data for a plurality of projection angles using each detector array; and rebinning the projection data for each selected phase of the object.

15. A method in accordance with claim 1 wherein collecting at least one segment of projection data for each selected phase of the object during each rotation of each x-ray source comprises the steps of:

detecting an arrhythmic cycle of the object; and collecting replacement projection data for the projection data collected during the arrhythmic cycle.

16. A computed tomography (CT) imaging system for generating an image of an object, the imaging system including at least one x-ray detector array and at least one rotating x-ray source projecting an x-ray beam, the imaging system configured to:

identify a physiological cycle of the object, the cycle comprising a plurality of phases;

allow an operator to select at least one phase of the object;

collect at least one segment of projection data -for each selected phase of the object during each rotation of each the x-ray source;

generate a projection data set by combining the projection data segments;

generate a cross-sectional image of the entire object from the projection data set; and communicate the image or data associated with the image to a remote facility, the remote facility providing remote services over a network.

17. An imaging system in accordance with claim 16 wherein to generate a projection data set by combining the projection data segments, the imaging system configured to generate the projection data set for each the selected phase of the object by combining the projection data segments collected for the selected phase.

18. An imaging system in accordance with claim 16 wherein to collect at least one segment of projection data for each selected phase of the object during each rotation of each the x-ray source, the imaging system configured to:
rotate each the x-ray source a plurality of rotations; and
emitting an x-ray beam from each the x-ray source toward each the x-ray detector array from a plurality of projection angles.

19. An imaging system in accordance with claim 18 wherein to collect at least one segment of projection data for each selected phase of the object during each rotation of each the x-ray source, wherein, the imaging system further configured to collect each segment of projection data for the selected phase from a different projection angle.

20. An imaging system in accordance with claim 19 wherein to collect each segment of projection data for the selected phase from a different projection angle, the system configured to alter a rotational speed of each the x-ray source.

21. An imaging system in accordance with claim 20 wherein to emit an x-ray beam from each the x-ray source toward each the x-ray detector array from plurality of projection angles, the imaging system configured to emit an x-ray beam from each the x-ray source for a determined imaging temporal period.

22. An imaging system in accordance with claim 21 wherein the rotational speed of each x-ray source is determined in accordance with:

$$V_G = \frac{1}{(T_c \pm (n * R_t))}$$

(in revolutions per second)
where:
Tc is the cardiac cycle time in seconds;
n is an integer constant; and
Rt is the determined imaging temporal period in seconds.

23. An imaging system in accordance with claim 21 wherein to collect at least one segment of projection data for each cycle of the object, the imaging system configured to alter the rotational speed of each the x-ray source in accordance with:

$$V_G = \left( \frac{180 + \frac{y}{n}}{180 * w} \right)$$

(in rotations per second)
where:
w is a period of a physiological cycle (in seconds),
γ y is a projection angle range for a complete projection data set (in degrees), and
n is a selected integer number of cycles to collect a complete projection data set.

24. An imaging system in accordance with claim 21 wherein to collect at least one segment of projection data for each cycle of the object, the imaging system configured to alter the rotational speed of each the x-ray source in accordance with:

$$Y_G = \left( \frac{360 + \frac{y}{n}}{360 * w} \right)$$

(in rotations per second)
where:
w is a period of a physiological cycle (in seconds),
γ is a projection angle range for a complete projection data set (in degrees), and
n is a selected number of cycles to collect a complete projection data set.

25. An imaging system in accordance with claim 16 wherein the imaging system includes a first x-ray source, a second x-ray source, a first detector array and a second detector array.

26. An imaging system in accordance with claim 16 wherein to allow an operator to select at least one phase of the object, the imaging system configured to:
allow the operator to select a first selected phase of the object; and
allow the operator to select a second selected phase of the object.

27. An imaging system in accordance with claim 16 wherein to identify a physiological cycle of the object, the imaging system configured to identify a physiological cycle of a heart comprising a systolic phase and a diastolic phase.

28. An imaging system in accordance with claim 16 wherein to identify a physiological cycle of the object, the imaging system configured to identify a physiological cycle of a respiratory system.

29. An imaging system in accordance with claim 16 wherein to generate a projection data set by combining the projection data segments, the imaging system configured to:
rotate each the x-ray source a plurality of projection angles;
collect projection data for a plurality of projection angles using each the detector array; and
rebin the projection data for each selected phase of the object.

30. An imaging system in accordance with claim 16 wherein to collect at least one segment of projection data for each selected phase of the object during each rotation of each the x-ray source, the imaging system configured to:
detect an arrhythmic cycle of the object; and
collect replacement projection data for the projection data collected during the arrhythmic cycle.

* * * * *

UNITED STATES PATENT AND TRADEMARK OFFICE
CERTIFICATE OF CORRECTION

PATENT NO. : 6,408,043 B1
DATED : June 18, 2002
INVENTOR(S) : David Lin et al.

It is certified that error appears in the above-identified patent and that said Letters Patent is hereby corrected as shown below:

Column 5,
Line 11, before "rotations" insert -- of --;
Line 26, after "period," delete "$R_1$" and insert -- $R_t$ --;

Column 8,
Line 27, after "complete" delete "rotation" and insert -- rotations --;

Column 9,
Line 28, after "the" delete "canner" and insert -- scanner --;
Line 33, after "circuitry" delete "or" and insert -- for --;

Column 11,
Line 61, after "Java," delete "per" and insert -- perl --;

Column 13,
Line 34, after "Alternatively," delete "w here" and insert -- where --;

Column 17,
Line 24, delete "x- ray" and insert -- x-ray --;
Line 52, after "$\gamma$" delete "y".

Signed and Sealed this

Eighteenth Day of February, 2003

JAMES E. ROGAN
*Director of the United States Patent and Trademark Office*